(12) United States Patent
Sun et al.

(10) Patent No.: US 10,874,748 B2
(45) Date of Patent: Dec. 29, 2020

(54) INTERVENTION FOR TENDINOPATHY

(71) Applicants: Albert Einstein College of Medicine, Bronx, NY (US); Icahn School of Medicine at Mount Sinai, New York, NY (US); Montefiore Medical Center, Bronx, NY (US)

(72) Inventors: Hui B. Sun, Chappaqua, NY (US); Evan L. Flatow, New York, NY (US); Tony Wanich, Englewood Cliffs, NJ (US); Konrad Gruson, New York, NY (US); Nelly Andarawis-Puri, New York, NY (US)

(73) Assignees: Albert Einstein College of Medicine, Bronx, NY (US); Icahn School of Medicine at Mount Sinai, New York, NY (US); Montefiore Medical Center, Bronx, NY (US)

( * ) Notice: Subject to any disclaimer, the term of this patent is extended or adjusted under 35 U.S.C. 154(b) by 92 days.

(21) Appl. No.: 15/577,470

(22) PCT Filed: Jun. 10, 2016

(86) PCT No.: PCT/US2016/036786
§ 371 (c)(1),
(2) Date: Nov. 28, 2017

(87) PCT Pub. No.: WO2016/201162
PCT Pub. Date: Dec. 15, 2016

(65) Prior Publication Data
US 2018/0148686 A1    May 31, 2018

Related U.S. Application Data

(60) Provisional application No. 62/174,005, filed on Jun. 11, 2015.

(51) Int. Cl.
| | | |
|---|---|---|
| *A61K 48/00* | (2006.01) |
| *C12N 5/077* | (2010.01) |
| *A61P 21/00* | (2006.01) |
| *A61K 45/06* | (2006.01) |
| *A61L 27/38* | (2006.01) |

(52) U.S. Cl.
CPC .............. *A61K 48/00* (2013.01); *A61K 45/06* (2013.01); *A61K 48/0091* (2013.01); *A61L 27/386* (2013.01); *A61P 21/00* (2018.01); *C12N 5/066* (2013.01); *C12N 2501/60* (2013.01); *C12N 2510/02* (2013.01)

(58) Field of Classification Search
CPC ................................ A61K 48/00; C12N 5/066
See application file for complete search history.

(56) References Cited

PUBLICATIONS

Wysoczynki et al. Circ Res 123(2):138-158, 2018, printed pp. 1-20. (Year: 2018).*
Liu and Wong. Muscles,Ligaments and Tendons Journal 2(3):163-16, 2012. (Year: 2012).*
PCT International Search Report and Written Opinion, dated Oct. 3, 2016 in connection with PCT International Application No. PCT/US2016/36786, 12 pages.
Saad F et al., entitled "CITED2 rejuvenates aged tendon stem/progenitor Cells (TSPC) and repaired aged tendon tissue through a novel paracrine mechanism," 2014 ORS Annual Meeting Poster No. 0115 [Retrieved on Sep. 4, 2016] Retrieved from website http://www.ors.org/Transactions/60/0115.pdf.
Zhou Z et al., entitled "CITED2 is essential for tendon-dervied stem cell self-renewal," ORS Annual Meeting Paper No. 49. 2011 [Retrieved on Sep. 4, 2016] Retrieved from website http://www.ors.org/Transactions/57/0049.pdf.
Sun H B et al., entitled "Bilogy and Mechano-Response of Tendon Cells: Progress Overview and Perspectives," J Orthop Res, Jun. 1, 2015, vol. 33, No. 6, pp. 785-792.

* cited by examiner

*Primary Examiner* — Marcia S Noble
(74) *Attorney, Agent, or Firm* — Fox Rothschild LLP

(57) ABSTRACT

Methods for treating tendinopathy and tendonitis and for preventing tendinopathy are disclosed.

6 Claims, 23 Drawing Sheets
Specification includes a Sequence Listing.

Experimental design

Nude rat tendon injury model

- Male, 10-12 months old, nude rats n=3/group
- Complete transverse Achilles transection
  <sub>Okamoto et al. JBJS, 2010</sub>

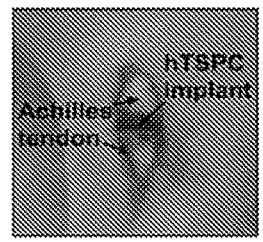

Experimental protocol

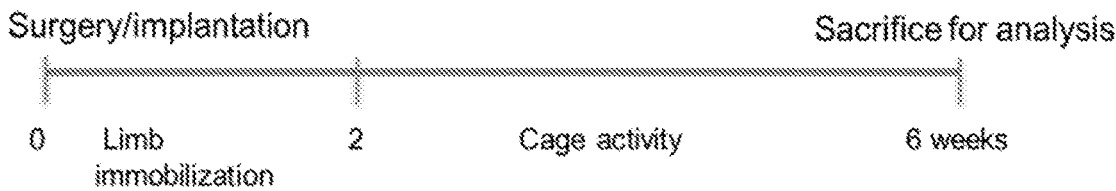

Surgery/implantation — Sacrifice for analysis

0 — Limb immobilization — 2 — Cage activity — 6 weeks

TSPC reprogramming and implantation

$10^6$ Human TSPCs labeled with PKH26 fluorescent dye and implanted in fibrin hydrogel

Experimental groups
- Aged human TSPCs transduced with CITED2
- Aged human TSPCs transduced with control vector
- Young human TSPCs
- No TSPCs

FIG. 1

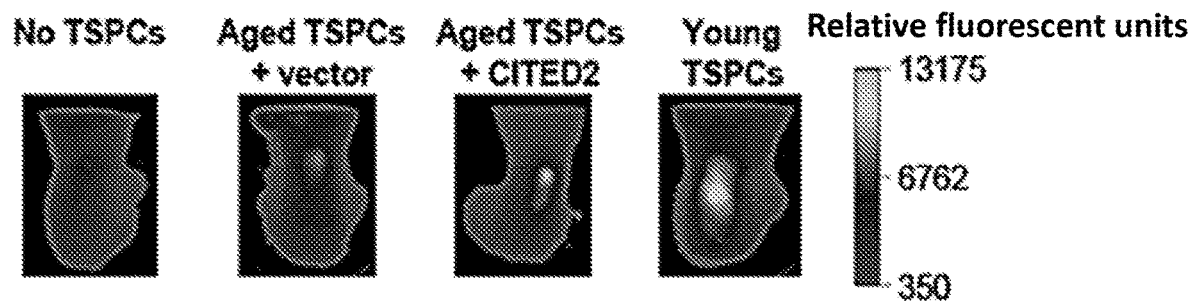
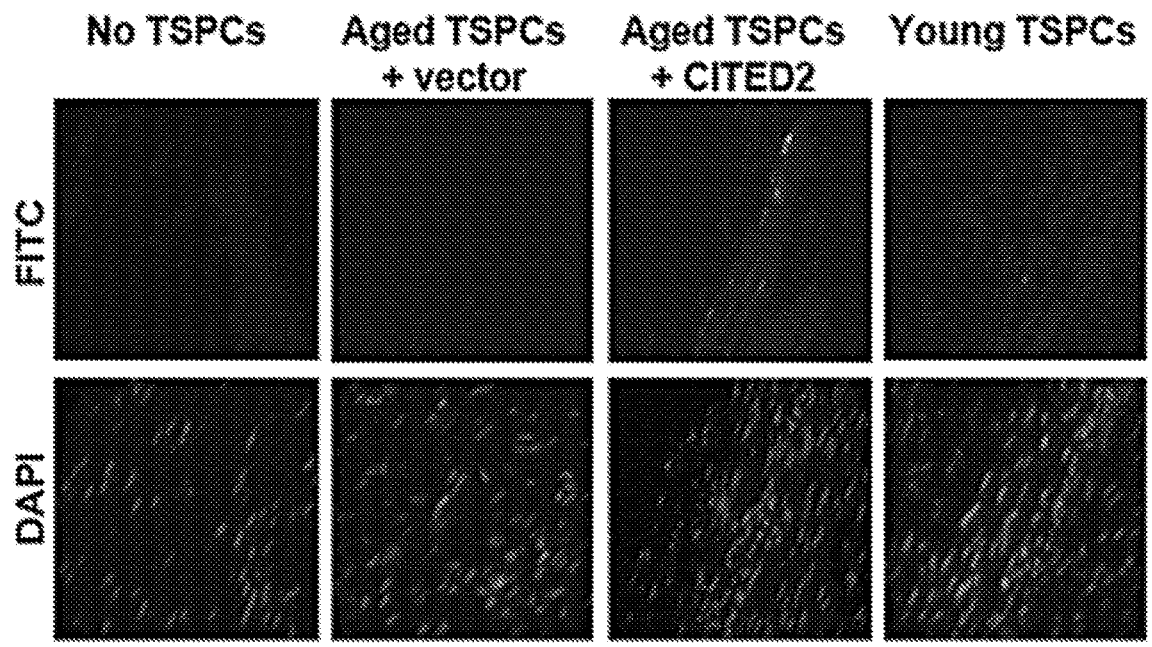
FIG. 2

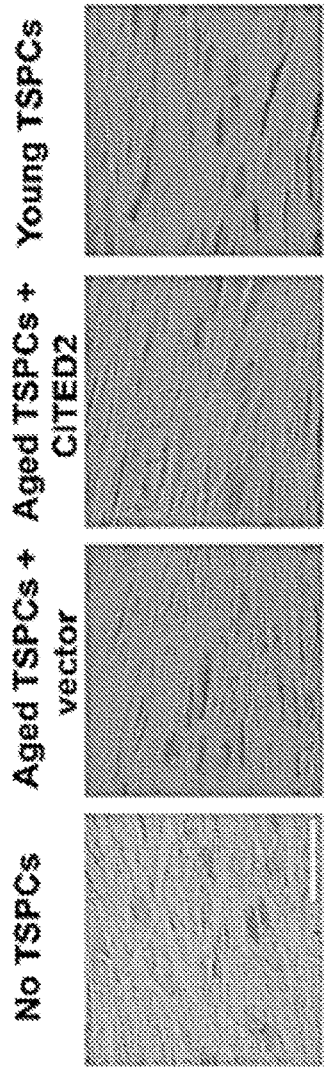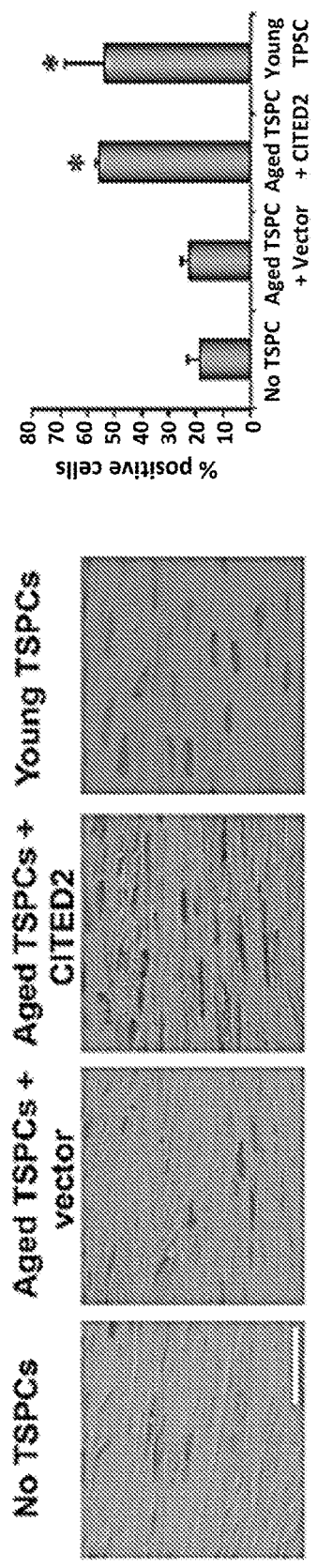
Upregulates expression of tenocyte markers
Scleraxis — early tenocyte differentiation marker
Tenomodulin — late/mature tenocyte differentiation marker
Scale bar = 50μM
FIG. 6

Reduces expression of senescent marker in repaired tissue
Fucosidase A1 (FucA1; cell senescence marker)
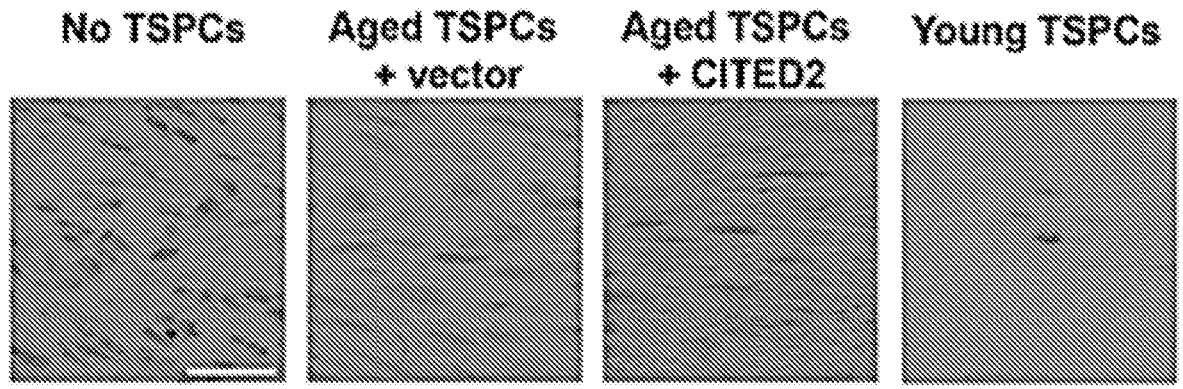
Scale bar = 50µM
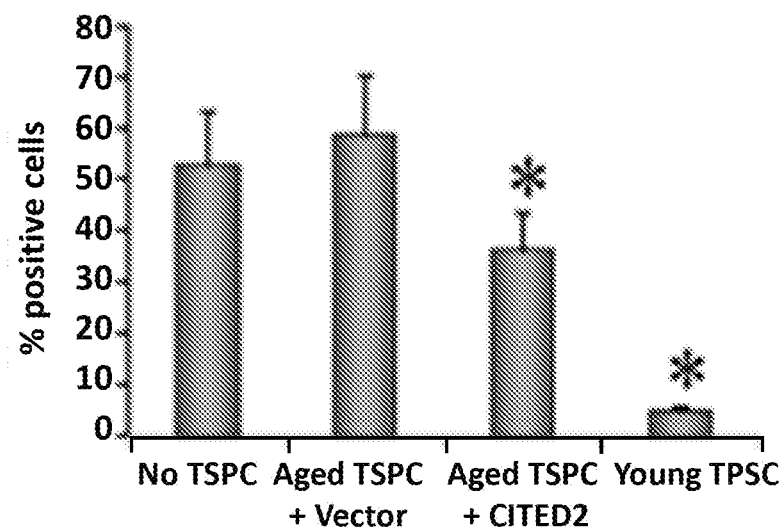
(*: p<0.05)
FIG. 7

Reduced proliferation rate and increased cell cycle arrest
WT vs Cited2+/-
Proliferation rate
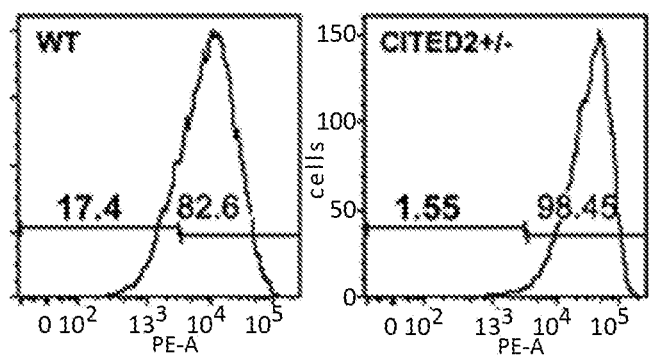
Human TSPCs CITED2 knockdown
Proliferation rate
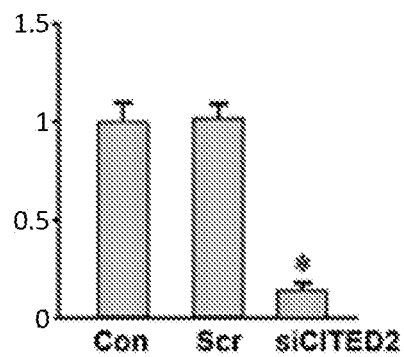
FIG. 13A Reduced proliferation rate and increased cell cycle arrest
Cell cycle analysis
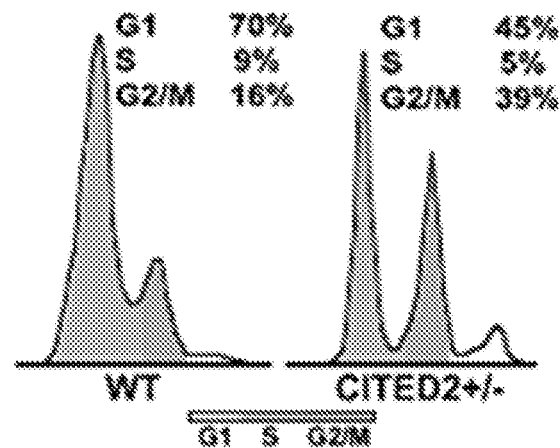
Cell cycle analysis
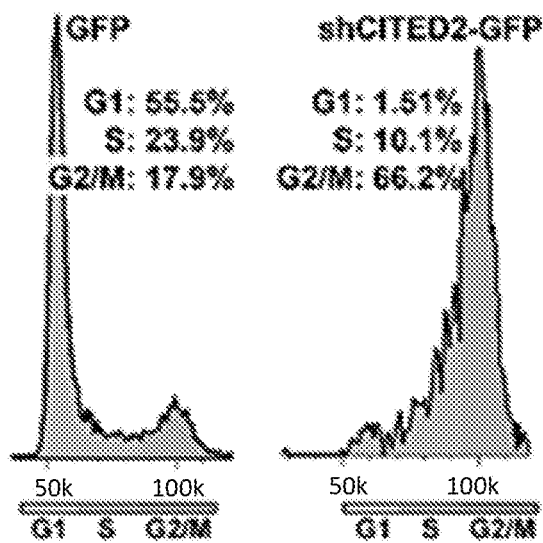
FIG. 13B

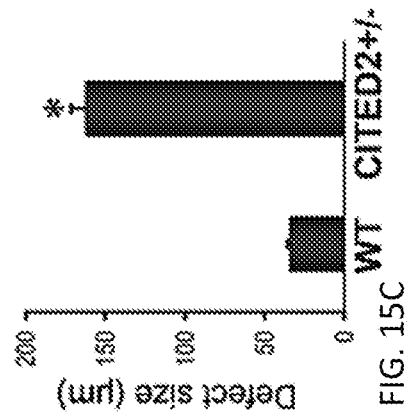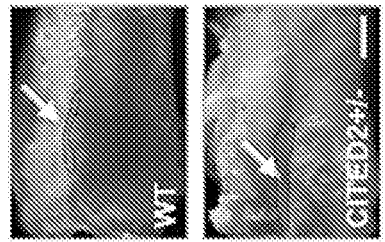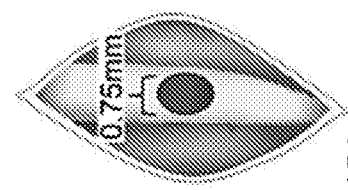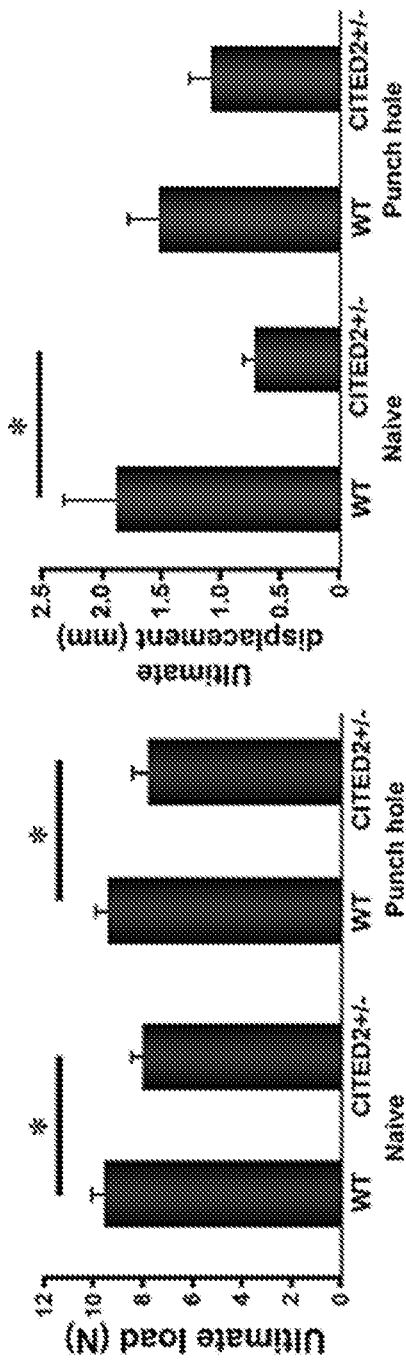
FIG. 15A
FIG. 15B
FIG. 15C
FIG. 15D
FIG. 15E

US 10,874,748 B2

INTERVENTION FOR TENDINOPATHY

CROSS-REFERENCE TO RELATED APPLICATIONS

This application is a U.S. national stage entry under 35 U.S.C. § 371 of PCT International Patent Application No. PCT/US2016/036786, filed Jun. 10, 2016, which claims benefit of U.S. Provisional Application No. 62/174,005, filed Jun. 11, 2015, the contents of each of which are incorporated herein by reference into the subject application.

STATEMENT OF GOVERNMENT SUPPORT

This invention was made with government support under grant numbers AG039561 awarded by the National Institutes of Health. The government has certain rights in the invention.

BACKGROUND OF THE INVENTION

Throughout this application various publications are referred to in brackets. Full citations for these references may be found at the end of the specification. The disclosures of these publications, and of all patents, patent application publications and books referred to herein, are hereby incorporated by reference in their entirety into the subject application to more fully describe the art to which the subject invention pertains.

The most common treatment for tendon ruptures is surgery. For tendinopathies, clinical treatments are less well-established. Possible treatments include icing, massage therapy, eccentric exercise, NSAIDs, ultrasound therapy, LIPUS, electrotherapy, taping, sclerosing injections, blood injection, glyceryl trinitrate patches, and extracorporeal shockwave therapy (ESWT). If not treated, tendinopathies can result in tendon rupture.

Herein is disclosed a method for using cells expressing CITED2 to treat tendinopathies and tendonitis.

SUMMARY OF THE INVENTION

A method is provided of treating a soft tissue degradation pathology in a subject comprising administering to the subject an amount of mesenchymal stem cells (MSCs) or tendon stem/progenitor cells (TSPCs) transfected to express CREB-binding protein/p300-interacting protein 2 (CITED2) to the subject effective to treat a soft tissue degradation pathology in a subject.

Also provided is a method of treating a tendinopathy in a subject comprising administering to the subject an amount of mesenchymal stem cells (MSCs) or tendon stem/progenitor cells (TSPCs) transfected to express CREB-binding protein/p300-interacting protein 2 (CITED2) to the subject effective to treat a tendinopathy in a subject.

Also provided is a method of determining the likelihood a tendon will suffer an injury or rupture due to aging comprising obtaining a sample of a tendon and quantifying the level of CREB-binding protein/p300-interacting protein 2 (CITED2) in the sample, and comparing the level to a predetermined control level for the sample size, and determining the likelihood the tendon will suffer an injury or rupture due to aging, wherein a level of CITED 2 quantitated in excess of the predetermined control level indicates that the tendon is not likely to suffer an injury or rupture due to aging and a level of CITED 2 quantitated below the predetermined control level indicates that the tendon is likely to suffer an injury or rupture due to aging.

A method of determining the level of CREB-binding protein/p300-interacting protein 2 (CITED2) in a tendon comprising
obtaining a sample of a tendon and
quantifying the level of CREB-binding protein/p300-interacting protein 2 (CITED2) in the sample, and comparing the level to a predetermined control level for the sample size, and determining whether the level of CITED 2 quantitated is in excess of the predetermined control level or whether the level of CITED 2 quantitated is below the predetermined control level.

A method is provided for (i) improving integration between repaired and native tissue in a tendon, (ii) improving matrix organization in a tendon, (iii) promoting teno-differentiation phenotype in a tendon, (iv) reducing age-related senescence markers of aged implanted cells and cells from adjoining host tissue in a tendon, (v) elevating TGF-β and CTGF in a repaired tendon tissue, or (vi) treating a rupture in a tendon,
wherein the tendon is in a subject, comprising administering to the subject an amount of mesenchymal stem cells (MSCs) or tendon stem/progenitor cells (TSPCs) transfected to express CREB-binding protein/p300-interacting protein 2 (CITED2) to the subject effective to (i) improve integration between repaired and native tissue in a tendon, (ii) improve matrix organization in a tendon, (iii) promote teno-differentiation phenotype in a tendon, (iv) reduce age-related senescence markers of aged implanted cells and cells from adjoining host tissue in a tendon, (v) elevate TGF-β and CTGF in a repaired tendon tissue, or (vi) treat a rupture, respectively, in a tendon in a subject.

BRIEF DESCRIPTION OF THE DRAWINGS

FIG. 1: Experimental design to evaluate therapeutic potential of CITED2 reprogramming of aged TSPCs.

FIG. 2: Localization of human TSPCs in implanted wound site detected by imaging of fluorescently labelled TPSCs at 2 weeks following implantation, or by fluorescent detection of human chromosomes at 6 weeks after implantation.

FIG. 6: Immunohistochemistry of tenocyte markers Scleraxis (Scx) and Tenomodulin (Tnmd). Injury implanted with Aged TSPCs+CITED2 or young TPSCs exhibited higher levels of Scx and Tnmd compared to the other groups. *p<0.05 vs No TSPC group. One-way ANOVA with Tukey's post-hoc test. n=3/group.

FIG. 7: Immunohistochemistry of senescence marker Fucosidase A1 (FucA1) in repaired tissue. Injury implanted with Aged TSPCs+CITED2 or Young TSPCs exhibited lower levels of FucA1 in the repaired tissue. *p<0.05 vs no TPSC group. One-way ANOVA with Tukey's post-hoc test. n=3/group.

FIG. 13A and FIG. 13B: CITED2 knockdown reduced proliferation rate and increased cell cycle arrest of TSPCs.

FIGS. 15A-15E: CITED2 knockdown impaired tendon healing, following a window transection wound in patellar tendons in mice.

DETAILED DESCRIPTION OF THE INVENTION

Figure 3:
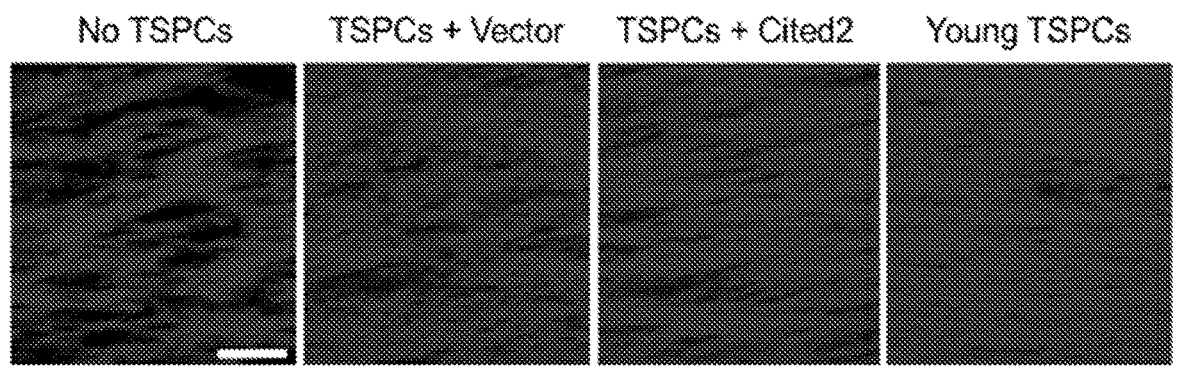
FIG. 3: Collagen fibril organization. Young TSPCs and TSPCs+CITED2 exhibited a more aligned collagen structure compared to tendons with no TSPCs and TSPCs transfected with a vector only.
Figure 4:
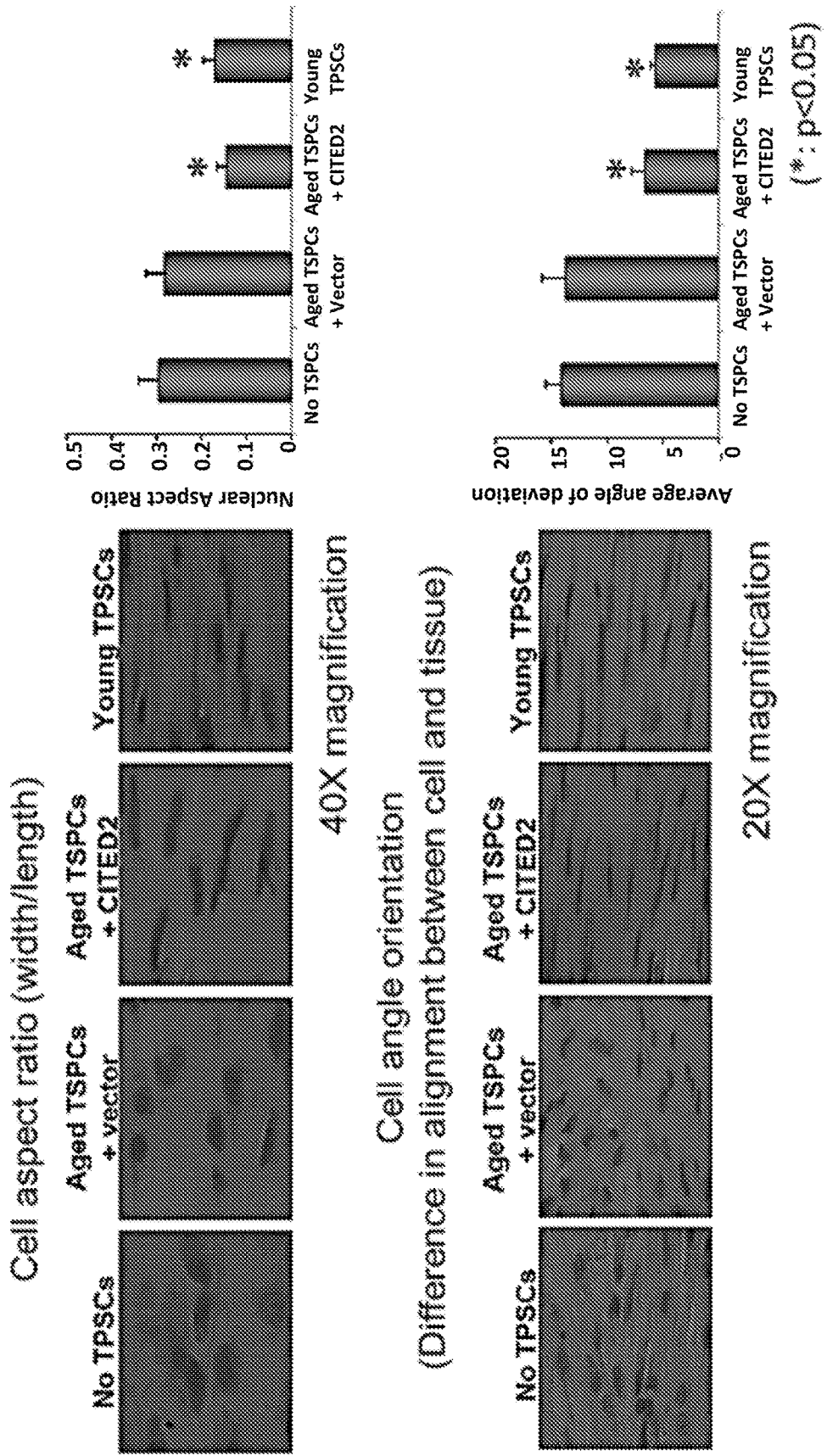
FIG. 4: Cell aspect ratio (width/length of cell, top) and cell angle orientation (difference in alignment between cell and tissue, bottom). Aged TSPCs+CITED2 and Young TSPCs showed a more elongated cell structure and better cellular alignment compared to the other groups. *p<0.05 vs No TSPCs group. One-way ANOVA with Tukey's post hoc test. n=3/group.
Figure 5:
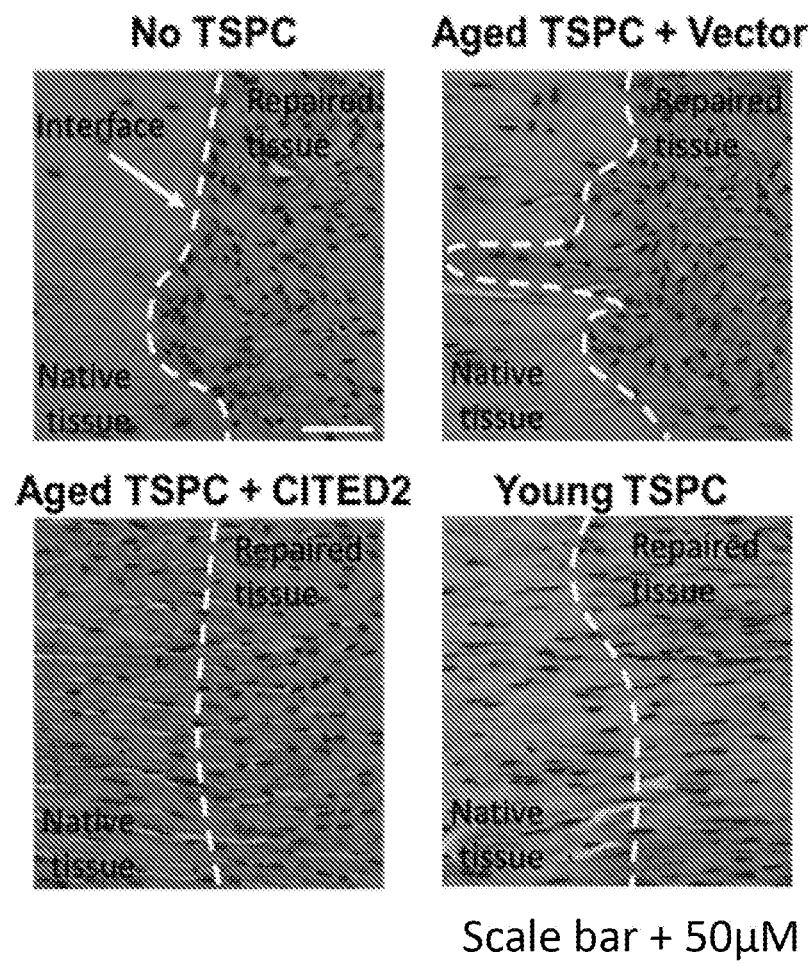
FIG. 5: H&E staining of interface between repaired tissue and host tissue. A more seamless integration was observed between the repaired tissue and native tissue in tendons implanted with Aged TSPCs+CITED2 and Young TSPCs. n=3/group.

Tendinopathy is a tendon disease associated with tendon aging and featured for inflammation and chronic injury. As evidenced herein (e.g. FIGS. 3-11), it is shown that increasing CITED2 levels (e.g. via gene transfer, cell-based therapy, chemical or physical induction) have a use as a tendinopathy treatment.

A method is provided of treating a soft tissue degradation pathology in a subject comprising administering to the subject an amount of mesenchymal stem cells (MSCs) or tendon stem/progenitor cells (TSPCs) transfected to express CREB-binding protein/p300-interacting protein 2 (CITED2) to the subject effective to treat a soft tissue degradation pathology in a subject. In an embodiment, the soft tissue is cartilage. In an embodiment, the soft tissue is a ligament. In an embodiment, the soft tissue is a tendon.

Also provided is a method of treating a tendinopathy in a subject comprising administering to the subject an amount of mesenchymal stem cells (MSCs) or tendon stem/progenitor cells (TSPCs) transfected to express CREB-binding protein/p300-interacting protein 2 (CITED2) to the subject effective to treat a tendinopathy in a subject.

In an embodiment of the methods described herein, the MSCs or TSPCs have been obtained from a human prior to their transfection to express CITED2. In an embodiment, the TSPCs are administered. In an embodiment, the MSCs are administered.

In an embodiment of the methods described herein, the MSCs or TSPCs have been obtained from a human biceps brachii tendon. Any other tendon in the human body is also an acceptable source of the cells.

The tendinopathy may be of an Achilles tendon, of a knee tendon or of an arm tendon.

In an embodiment of the methods described herein, the tendinopathy does not comprise a ruptured tendon. In an embodiment, the subject does not have a ruptured tendon.

In an embodiment of the methods described herein, the amount of the MSCs or TSPCs is administered directly to the tendon. In an embodiment of the methods described herein, the amount of the MSCs or TSPCs is implanted into, or directly adjacent to, the tendon.

In an embodiment of the methods described herein, the MSCs or TSPCs are obtained from an adult human prior to their transfection to express CITED2.

In an embodiment of the methods described herein, the tendinopathy comprises a tendinosis. In an embodiment of the methods described herein, the tendinopathy comprises a tendonitis.

In an embodiment of the methods described herein, the subject is a human.

Also provided is a method of determining the likelihood a tendon will suffer an injury or rupture due to aging comprising obtaining a sample of a tendon and quantifying the level of CREB-binding protein/p300-interacting protein 2 (CITED2) in the sample, and comparing the level to a predetermined control level for the sample size, and determining the likelihood the tendon will suffer an injury or rupture due to aging, wherein a level of CITED 2 quantitated in excess of the predetermined control level indicates that the tendon is not likely to suffer an injury or rupture due to aging and a level of CITED 2 quantitated in below the predetermined control level indicates that the tendon is likely to suffer an injury or rupture due to aging.

A method of determining the level of CREB-binding protein/p300-interacting protein 2 (CITED2) in a tendon comprising obtaining a sample of a tendon and quantifying the level of CREB-binding protein/p300-interacting protein 2 (CITED2) in the sample, and comparing the level to a predetermined control level for the sample size, and determining whether the level of CITED 2 quantitated is in excess of the predetermined control level or whether the level of CITED 2 quantitated is below the predetermined control level.

In the methods, the level of CITED2 in the sample can be quantified by determining by quantifying the amount of a polypeptide agent comprising an anti-CITED2 binding site that binds to the sample when contacted therewith. In an embodiment, the polypeptide agent comprising an anti- CITED2 binding site is an antibody or comprises an antigen-binding site of an antibody. In an embodiment, the agent comprising an anti-CITED2 binding site is labelled with a detectable marker molecule. Such markers are well known in the art, and include moieties such as radionuclides, fluorescent dyes, chemiluminescent agents, microparticles, nanoparticles, enzymes, colorimetric labels, magnetic labels, haptens, molecular beacons and aptamer beacons. Such detectable agents can also comprise antibodies or antibody fragments.

A method is provided for (i) improving integration between repaired and native tissue in a tendon, (ii) improving matrix organization in a tendon, (iii) promoting teno-differentiation phenotype in a tendon, (iv) reducing age-related senescence markers of aged implanted cells and cells from adjoining host tissue in a tendon, (v) elevating TGF-β and CTGF in a repaired tendon tissue, or (vi) treating a rupture in a tendon,
wherein the tendon is in a subject, comprising administering to the subject an amount of mesenchymal stem cells (MSCs) or tendon stem/progenitor cells (TSPCs) transfected to express CREB-binding protein/p300-interacting protein 2 (CITED2) to the subject effective to (i) improve integration between repaired and native tissue in a tendon, (ii) improve matrix organization in a tendon, (iii) promote teno-differentiation phenotype in a tendon, (iv) reduce age-related senescence markers of aged implanted cells and cells from adjoining host tissue in a tendon, (v) elevate TGF-β and CTGF in a repaired tendon tissue, or (vi) treat a rupture, respectively, in a tendon in a subject. Each of (i) to (v) are separable, individual embodiments of the method.

In an embodiment, the CITED2 is human CITED2. In an embodiment, and as used in the examples herein, the CITED2 contains is encoded by a cDNA of 1797 nucleotides (NM 001168388.2). In an embodiment, the CITED2 comprises the following sequence:

fection, which gave a slightly lower overexpression level (2-4-fold increase with similar result), and better fit the purpose of restoring the CITED2 levels in adult tissues to young/physiological levels. For the plasmid transfection, TSPCs were transfected with CITED2 cDNA with a GFP tag (CMV-CITED2-GFP) using Lipofectamine 2000 following manufacturer's instructions. For the adenovirus infection, the recombinant adenovirus containing the CITED2 coding region was produced by the AdEasy system according to the manufacturer's instructions.

Tendon rupture is a tear of the tendon that requires surgical intervention in an attempt to restore tissue function. This is a significant clinical issue since tendon is a tissue difficult to heal. In most cases, after a long healing period, only results in formation of scar tissue, with reduced function and pain, and revision surgeries are often required. The intervention disclosed herein can provide the stem cell source which is needed for such an acute injury condition. Furthermore, CITED2-reprogrammed implanted stem cells will have enhanced repair ability to shorten the healing time and lead to genuine tendon repair, rather than generation of scar tissue. The technique disclosed herein can treat tendon rupture.

On the other hand, tendinopathy does not exhibit overt tissue damage induced by an acute event as seen in tendon rupture. Tendinopathy is defined as chronic tendon degeneration, in most cases due to tendon overload, leading to microscopic collagen fiber failure and a failed healing response. Accumulating evidence suggests the pathology behind tendinopathy is the dysfunction of tendon stem cells. The method disclosed herein can modulate dysfunction of tendinopathy-related cell disorders through CITED2 reprogramming. Such modulation includes correcting impaired stem cell function due to aging and altered response to stresses such as overloading and inflammation. The intervention will increase the reparative source with healthy reprogrammed stem cells. Furthermore, the implanted cells

```
(NP_001161860.1)
                                                             (SEQ ID NO: 1)
  1    MADHMMAMNH  GRFPDGTNGL  HHHPAHRMGM  GQFPSPHHHQ  QQQPQHAFNA  LMGEHIHYGA

61    GNMNATSGIR  HAMGPGTVNG  GHPPSALAPA  ARFNNSQFMG  PPVASQGGSL  PASMQLQKLN

121    NQYFNHHPYP  HNHYMPDLHP  AAGHQMNGTN  QHFRDCNPKH  SGGSSTPGGS  GGSSTPGGSG

181    SSSGGGAGSS  NSGGGSGSGN  MPASVAHVPA  AMLPPNVIDT  DFIDEEVLMS  LVIEMGLDRI

241    KELPELWLGQ  NEFDFMTDFV  CKQQPSRVSC.
```

In an embodiment, the CITED2 comprises the following sequence:

are able to improve the tendinopathy condition by reducing inflammatory and stressed microenvironment, enhancing

```
(NP_001161860.2)
                                                             (SEQ ID NO: 2)
  1    MSGLEMADHM  MAMNHGRFPD  GTNGLHHHPA  HRMGMGQFPS  PHHHQQQQPQ  HAFNALMGEH

61    IHYGAGNMNA  TSGIRHAMGP  GTVNGGHPPS  ALAPAARFNN  SQFMGPPVAS  QGGSLPASMQ

121    LQKLNNQYFN  HHPYPHNHYM  PDLHPAAGHQ  MNGTNQHFRD  CNPKHSGGSS  TPGGSGGSST

181    PGGSGSSSGG  GAGSSNSGGG  SGSGNMPASV  AHVPAAMLPP  NVIDTDFIDE  EVLMSLVIEM

241    GLDRIKELPE  LWLGQNEFDF  MTDFVCKQQP  SRVSC
```

Two methods (adenovirus transduction and plasmid transfection) were used for increasing CITED2 expression in TSPCs. Initial work herein mainly used the adenovirus for infection, which yielded high levels of CITED2 (8-10-fold increase). The results were confirmed with plasmid transextracellular matrix synthesis. Furthermore, evidence also shows the reprogrammed stem cells can restore function of the dysfunctional resident (host) stem cells and other cells through a paracrine mechanism. Thus, the methods disclosed herein provide a new tendinopathy treatment.

As used herein, "treating" a tendinopathy means that one or more symptoms of the disease, such as the tendinopathy itself, tendon strength, inflammation thereof, or other parameters by which the disease is characterized, are reduced, ameliorated, inhibited, placed in a state of remission, or maintained in a state of remission. Tendinopathies may be broadly categorized into those which are a tendonitis and those which are tendonosis.

This invention will be better understood from the examples follow. However, one skilled in the art will readily appreciate that the specific methods and results discussed are merely illustrative of the invention as described more fully in the claims that follow thereafter.

Example 1

CITED2-reprogramming of aged stem cells for enhanced tendon rupture repair: It was investigated whether reprogramming of aged TSPCs would rejuvenate them and enhance their reparative ability. Wound healing was evaluated and the age-related and functional status of reparative and adjacent host tissue characterized of a full thickness rat Achilles wound created by laceration implanted with aged human TSPCs with or without CITED2 transfection in nude rats (FIG. 1).

Figure 8:
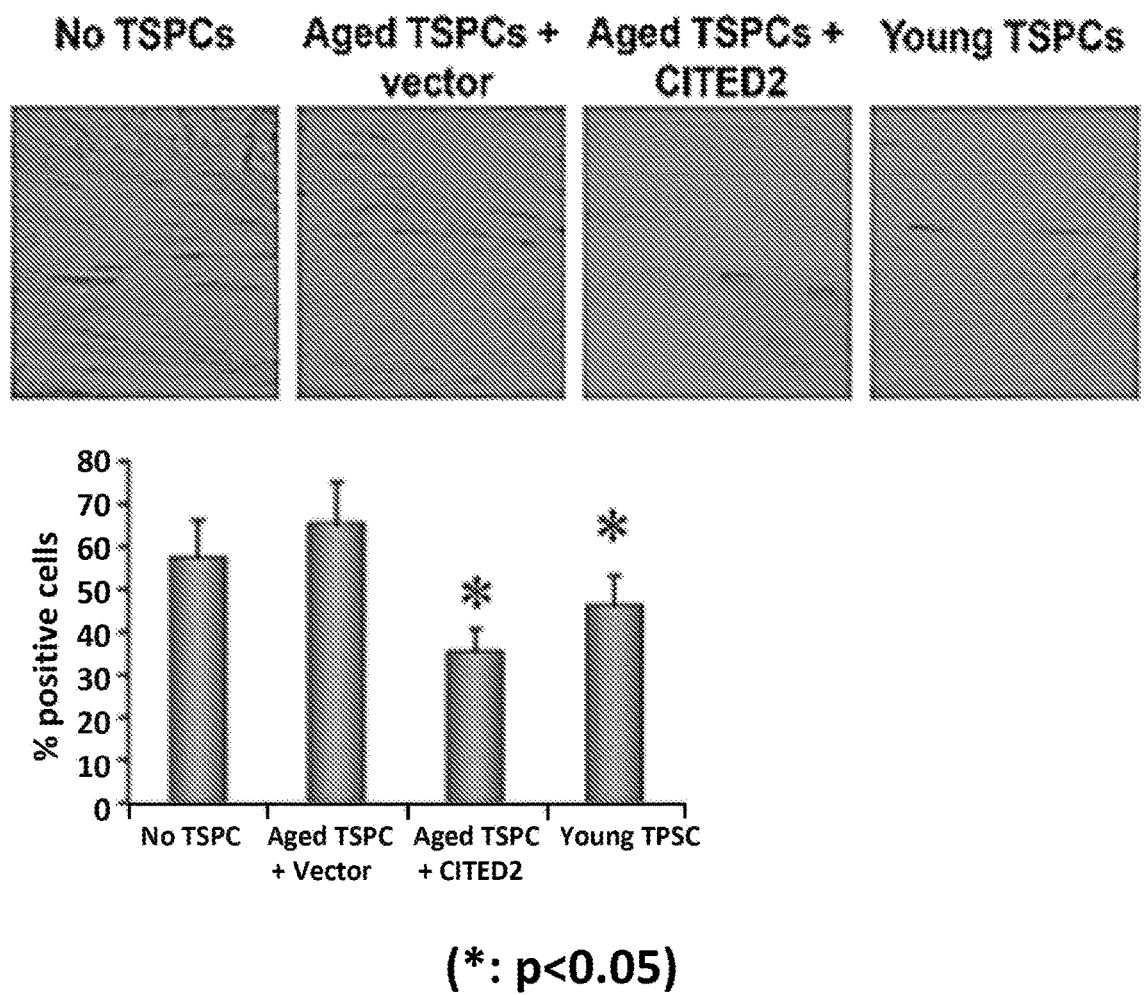
FIG. 8: Immunohistochemistry of senescence marker Fucosidase A1 in host tissue. Injury implanted with Aged TSPCs+CITED2 or Young TSPCs exhibited lower levels of FucA1 in the host rat tissue. *p<0.05 vs no TPSC group. One-way ANOVA with Tukey's post-hoc test. n=3/group.
Figure 9A:
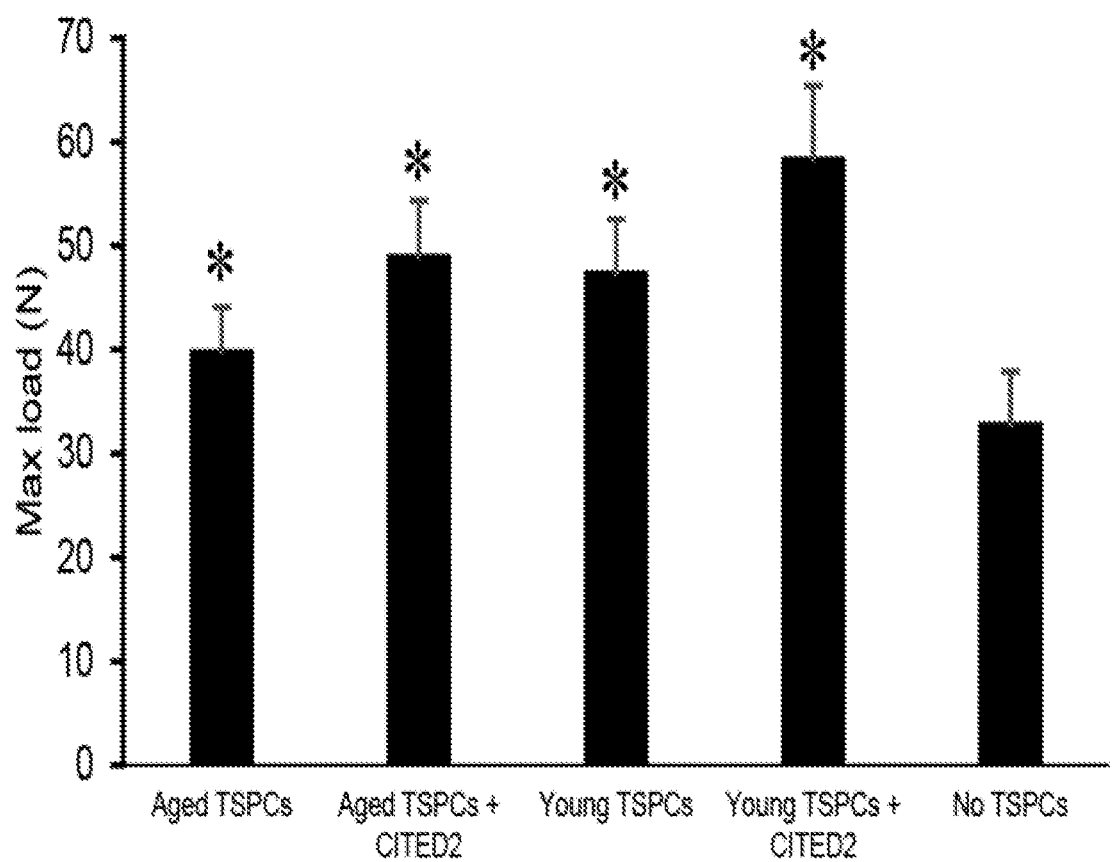
FIG. 9A-9C: (9A) Maximum load (newtons, N) and (9B) maximum stress (megapascals, MPa) of full thickness lacerated rat Achilles tendons implanted with young or aged human TSPCs with or without CITED2 reprogramming, or implanted with no TPSCs. *p<0.05 vs No TSPCs group. One-way ANOVA with Holm-Sidak's post-hoc test. n=5/group. (9C) Max load of full thickness lacerated rat Achilles tendons implanted with young or aged human TSPCs with or without CITED2 reprogramming, or implanted with no TPSCs. *p<0.05, vs indicated comparison. One-way ANOVA with Holm-Sidak's post-hoc test.
Figure 9B:
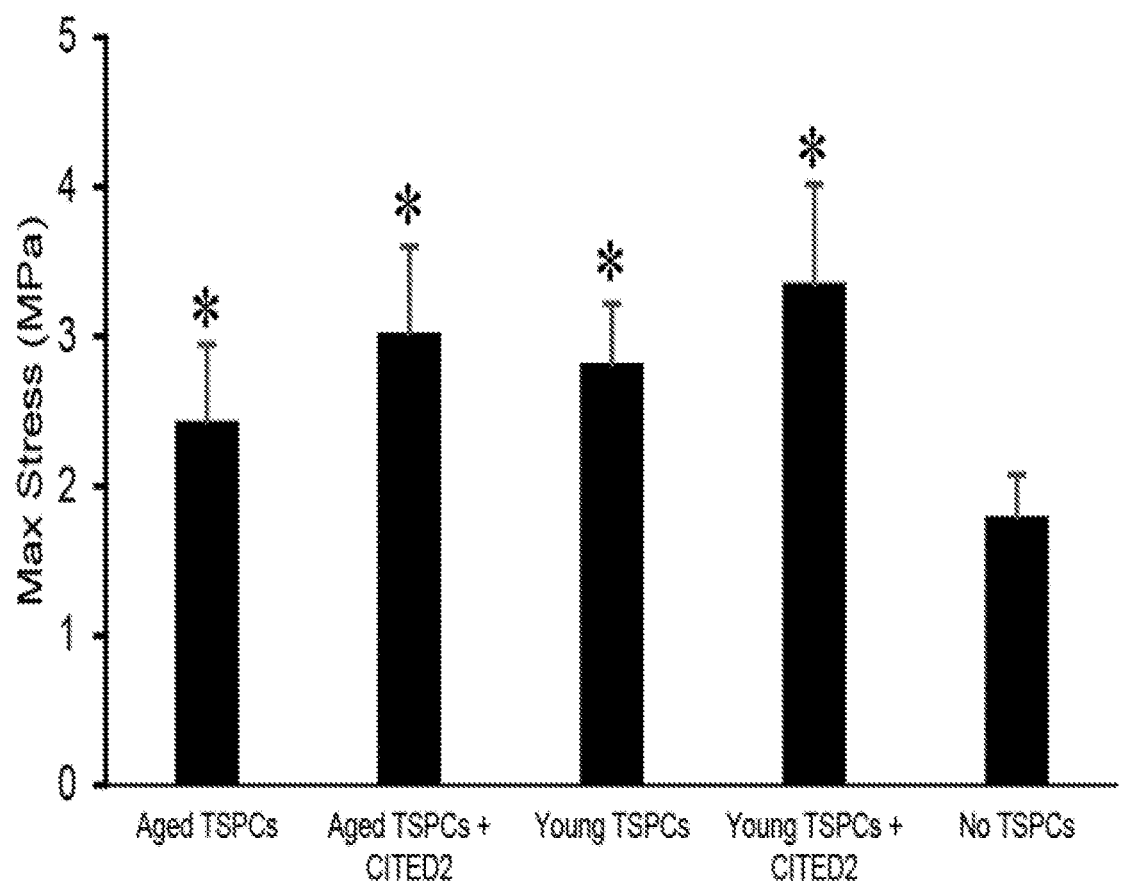
Figure 9C:
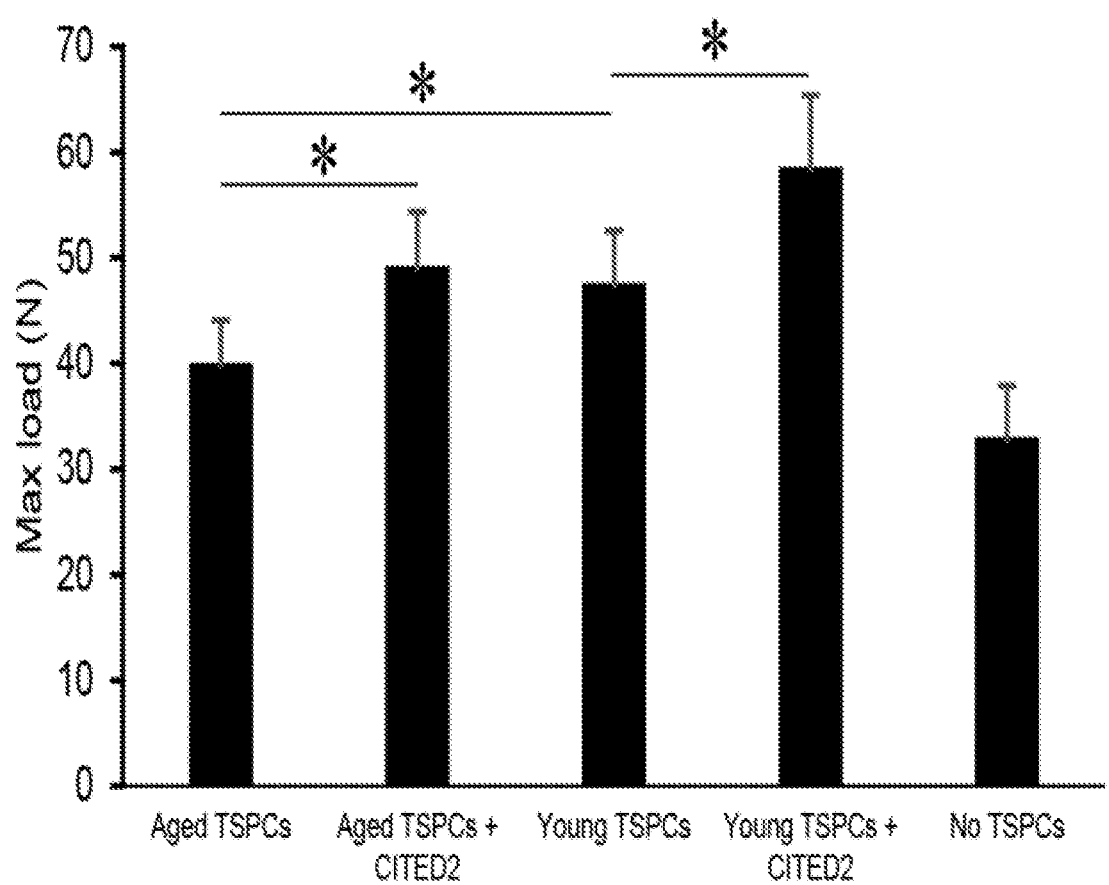
Figure 10:
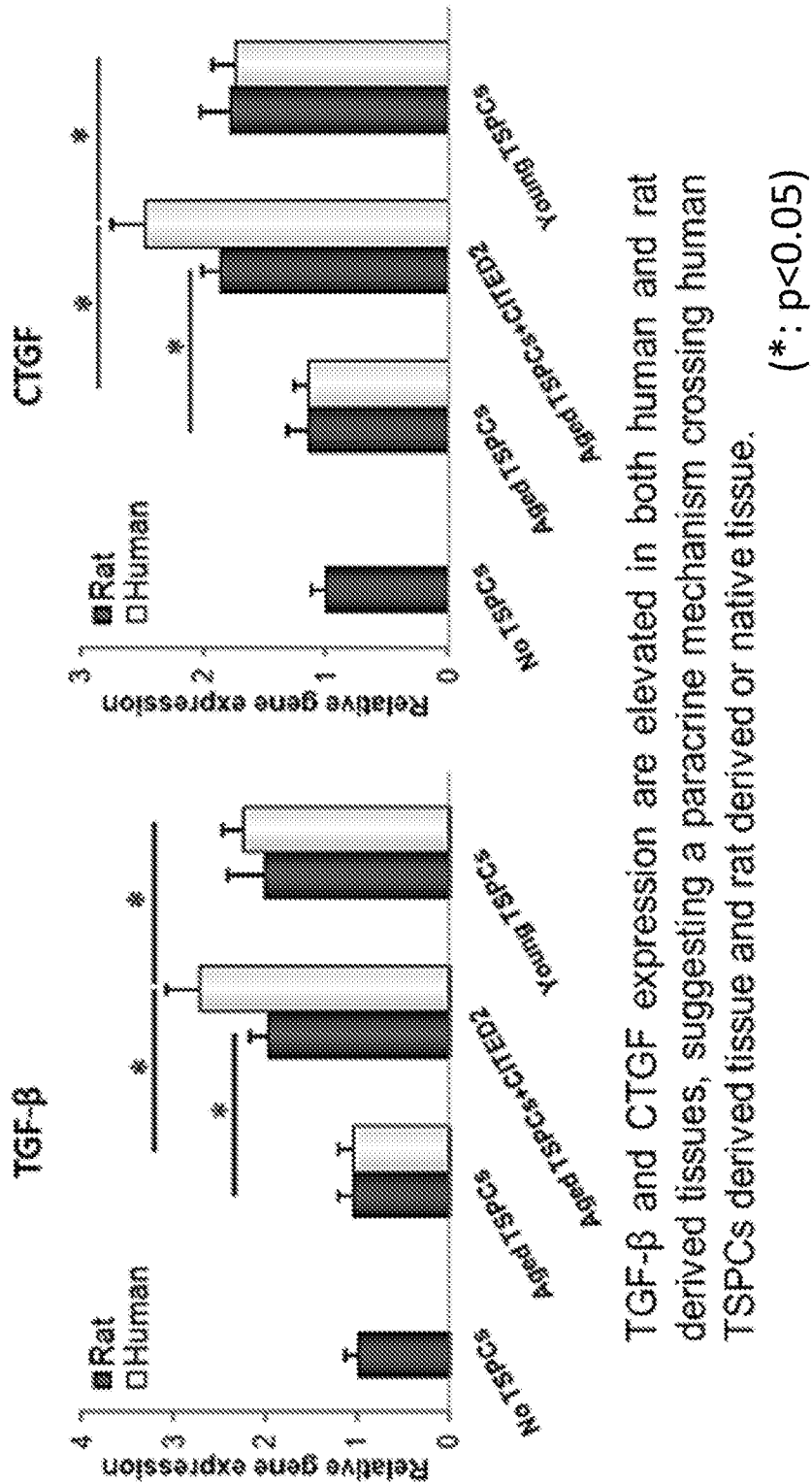
FIG. 10: mRNA expression of human and rat TGF-β and CTGF in the rat host tissue and in the repaired tissue derived from implanted human TPSCs. *p<0.05 vs indicated comparison. One-way ANOVA with Tukey's post-hoc test. n=3/group.

CITED2 reprogrammed aged human TSPCs localized to the wound site and integrated with the repaired tendon after implantation (FIG. 2). The tendons implanted with CITED2 reprogrammed aged human TSPCs: exhibited improved collagen fibril organization (FIG. 3), improved cell/matrix organization (FIG. 4), improved integration between the native and repaired tissue (FIG. 5), upregulated expression of tenocyte markers (FIG. 6), and reduced expression of senescent markers in the repaired tissue (FIG. 7). Notably, senescence levels were also reduced in the host tissue in tendons implanted with CITED2 reprogrammed human TSPCs and young TSPCs (FIG. 8). Furthermore, tendons implanted with TSPCs overexpressing CITED2 exhibited stronger mechanical properties (FIG. 9). Specifically, all the treated groups showed a higher maximum load (FIG. 9A) and maximum stress (FIG. 9B) compared to the no TSPCs implanted group. Furthermore, CITED2 reprogrammed TSPCs had a higher maximum load compared to the non-CITED2 reprogrammed TSPCs for both old and young cells (FIG. 9C), suggesting that CITED2 reprogramming enhances tendon healing by improving tendon mechanical properties. CITED2 rejuvenates aged TSPC and aged tendon tissue through not only direct (i.e. physical microenvironment support) but also indirect (autocrine/paracrine) mechanisms as evidenced by elevation of TGF-$\beta$ and CTGF in both human- and rat-derived components in the repaired tissue (FIG. 10).

These data show CITED2 reprogramming enhances TSPC reparative ability and promotes rejuvenation of aged human TSPCs and adjacent rat tissue. Based on the mechanical property testing, such as maximum load, CITED2 reprogramming increased the reparability of both old and young TSPCs, leading to a better wound healing outcome with stronger mechanical properties. Effects of CITED2 reprogramming are mediated, at least in part, through paracrine mechanisms.

In conclusion, CITED2-reprogrammed TSPCs are a solution for tendon injury repair and tendon aging. CITED2 reprogrammed human TSPCs:
  Improved integration between repaired and native tissue
  Improved matrix organization
  Promoted teno-differentiation phenotype
  Reduced age-related senescence marker of aged implanted cells and cells from adjoining host tissue
  Elevated TGF-$\beta$ and CTGF in both human and rat-derived repaired tissue.

Example 2

CITED2 as a tendon aging marker for status and susceptibility for tendinopathy and rupture: It was determined whether the level of CITED2 expression in TSPCs can be used as a tendon-aging marker. The relationship between level of CITED2 expression in TSPC and tendon aging in human tendons was established and then it was determined whether reduction of Cited2 leads to an aging phenotype in Cited2 haploinsufficient (Cited2+/−) mice.

Figure 11A:
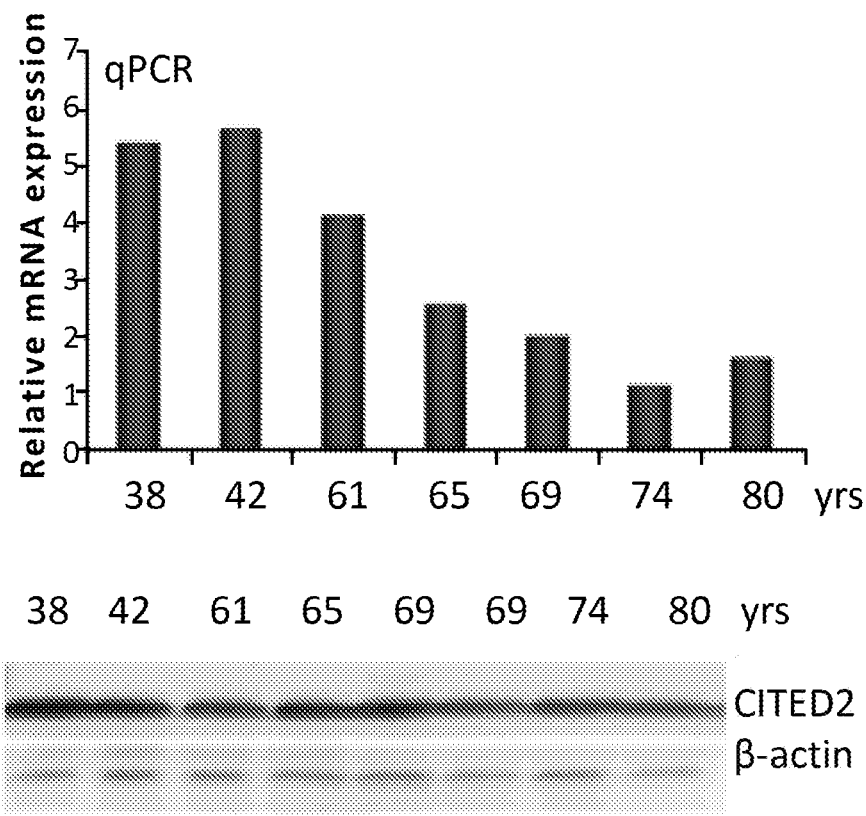
FIG. 11A-11E: Association between CITED2 expression (11A), Clonogenicity (11B), Nuclear aspect ratio (11C), Core area (11D), and percentage of senescent cells (11E) in TSPCs with increasing age in human.
Figure 11B:
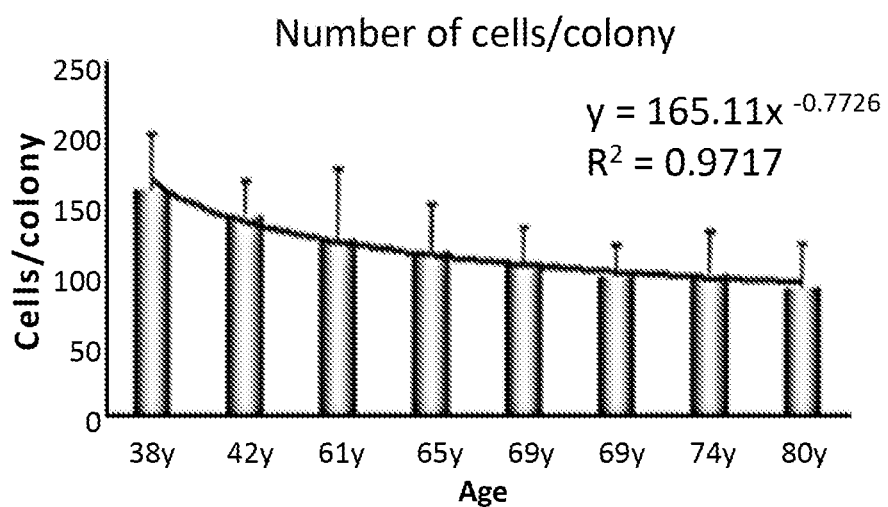
Figure 11C:
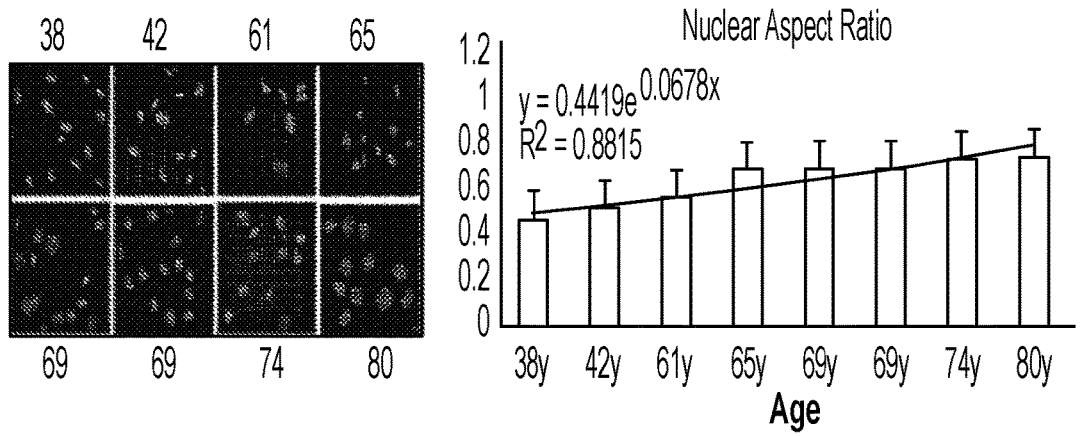
Figure 11D:
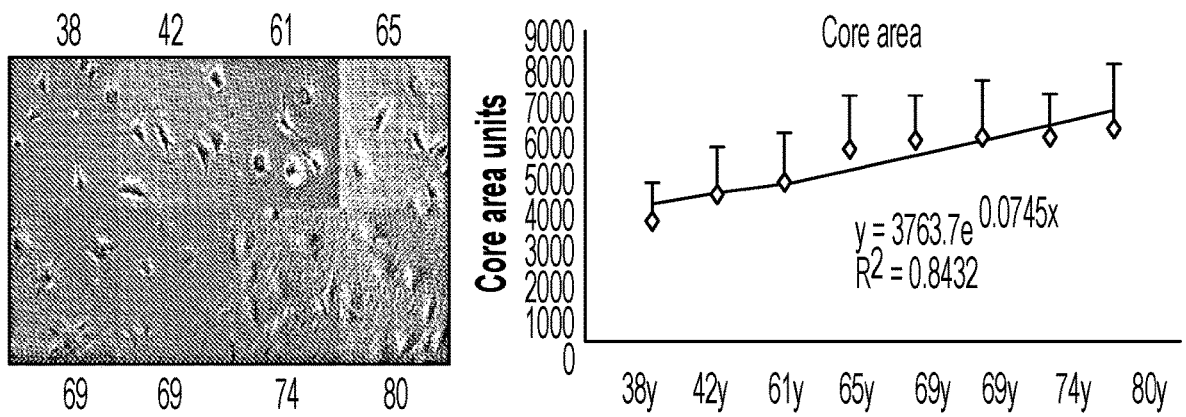
Figure 11E:
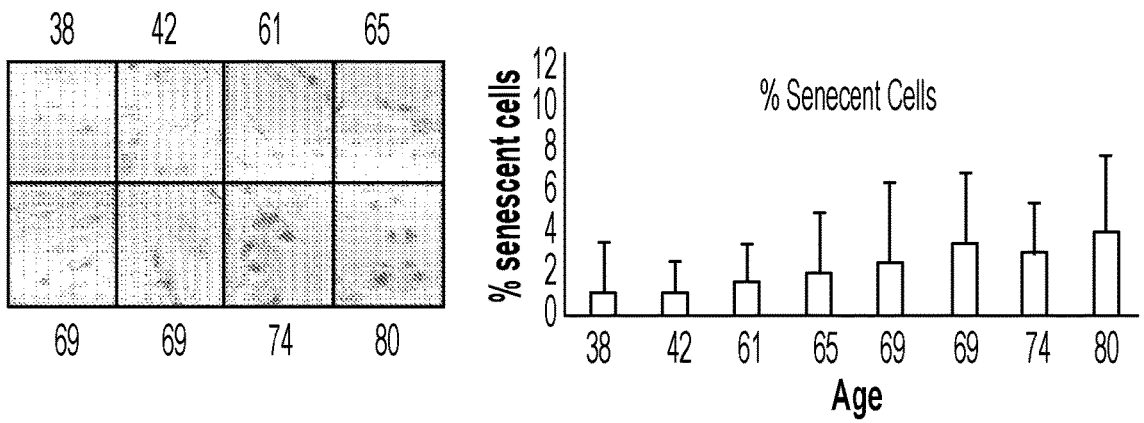

Levels of CITED2 expression in TSPCs at both the mRNA and protein levels is reversely associated with tendon aging in human (FIG. 11A). Furthermore, the number of cells/colony (FIG. 11B), nuclear aspect ratio (FIG. 11C), cell area (FIG. 11D), and percentage of senescent cells (FIG. 11E) of TSPC in vitro culture are also reversely associated with tendon aging.

Figure 12:
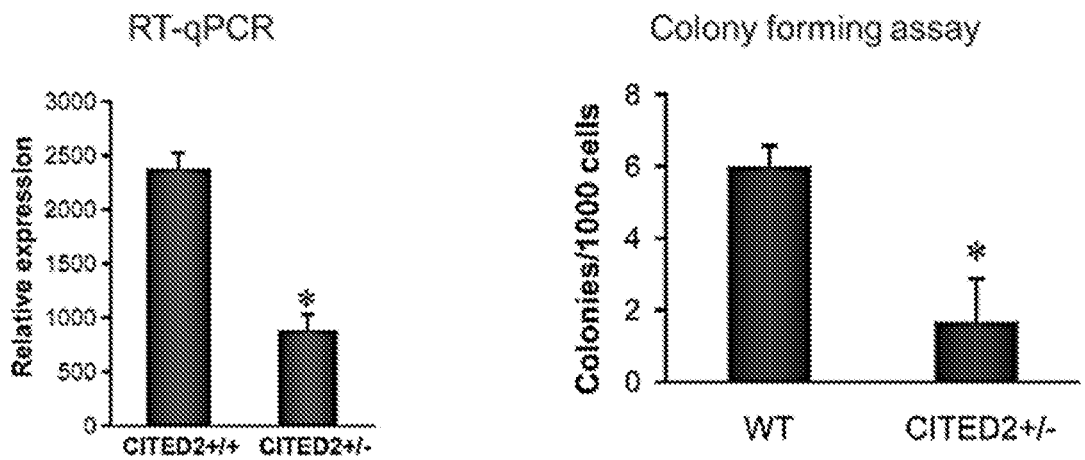
FIG. 12: CITED2 knockdown reduces colony forming ability of TSPCs.
Figure 14:
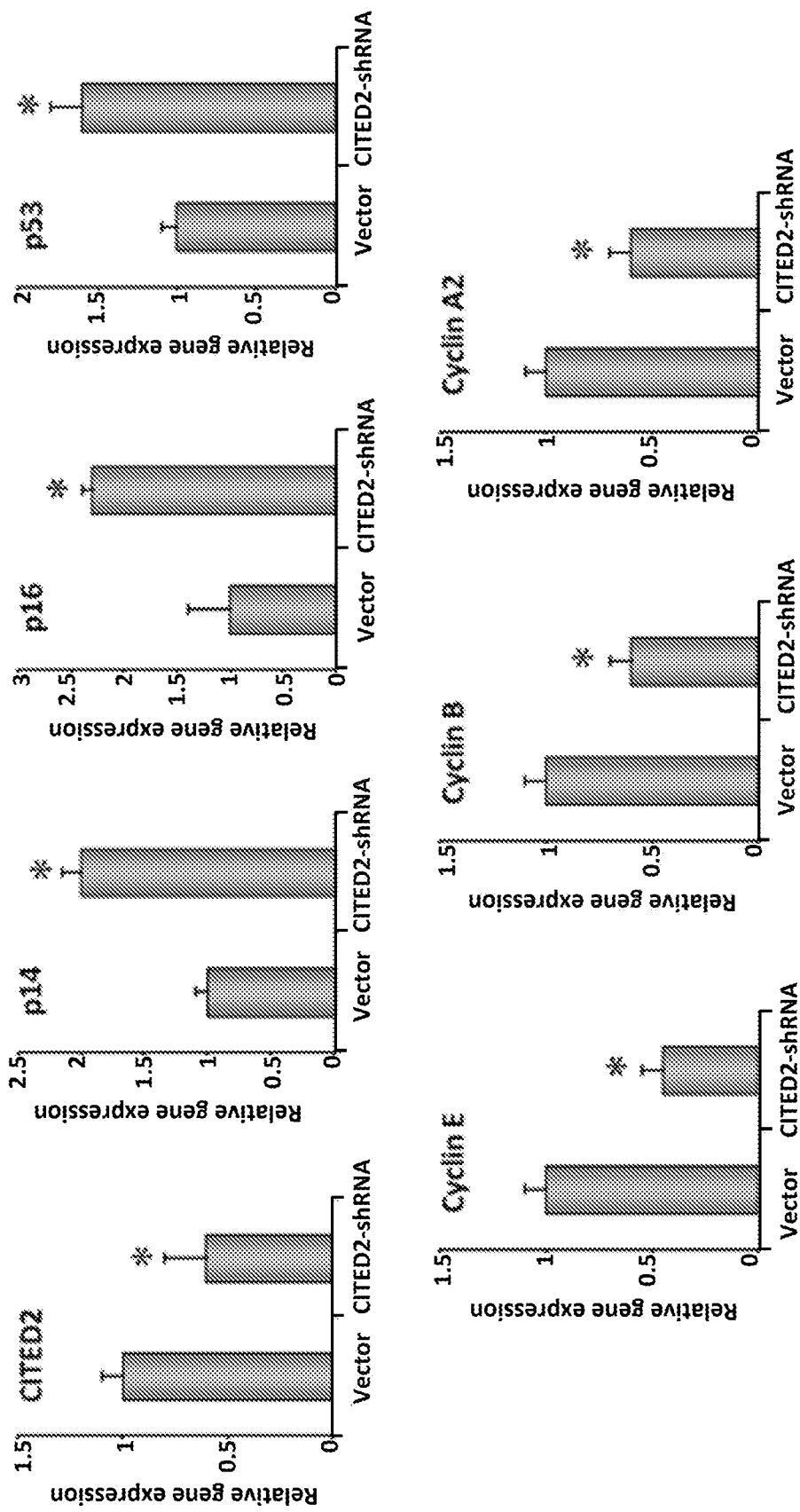
FIG. 14: CITED2 knockdown altered cell cycle related gene expression in TSPCs.

Cited2 haploinsufficient (Cited2+/−) mice exhibit aging phenotype, characterized by: a reduction in colony forming ability (FIG. 12), reduced proliferation rate and increased cell cycle arrest (FIG. 13), altered cell cycle related gene expression (FIG. 14), and impaired tendon healing (FIG. 15).

These data indicate CITED2 expression in TSPCs is reversely associated with tendon aging. Reductions of CITED2 leads to an aging phenotype including impaired wound healing, supporting that declining levels of CITED2 expression is a function of aging. Because aging is a risk factor for the onset of tendon wound injuries, CITED2 as a tendon aging marker may also be used as an indicator for the susceptibility for injury such as rupture and tendinopathy. In conclusion, CITED2 expression is associated with tendon aging that may be used as an indicator for tendon injury status and tendon injury susceptibility.

Methods

Tendon stem/progenitor cells (TSPCs) are identified and isolated as previously described (Zhou et al. Aging Cell, October; 9(5):911-5, 2010). Briefly, the fresh tendon tissue sample is cut into small pieces (1 mm×1 mm×1 mm or smaller). The tissues were digested with collagenase/dispase (Roche) in phosphate-buffered saline (PBS) at 37° C. for 2 hrs. The suspensions were centrifuged at 1,500 g for 15 min, and the supernatant was discarded. The remaining cell pellet was re-suspended in growth medium consisting of Dulbecco's modified Eagle's medium (DMEM) supplemented with 10% fetal bovine serum (FBS). A single-cell suspension was obtained by diluting the suspension and then cultured in 6-well plates at 37° C. with 5% $CO_2$. The culture medium is replaced with fresh medium every 2 days. After 8-10 days in culture, cell colonies are formed on the culture surface of the plate. The cells that exhibit a cobblestone shape are the TSPCs, and are designated as passage 0 (P0). The TSPCs may exhibit morphological characteristics and express stem cell markers such as octamer-binding transcription factor 4 (Oct-4), Stage-specific embryonic antigen-4 (SSEA-4), and nucleostemin, as assayed by reverse transcription real-time PCR at the mRNA level and immunocytochemistry staining or Western blot at the protein level. TSPCs showed the typical mesenchymal phenotype, with high expression of CD73, CD90 and CD105 and no expression of CD34 and CD45 by flow cytometry. TSPCs may exhibit morphological characteristics and express stem cell markers in culture for at least 10 passages (p10). P2 and P3 were used for the treatment in this application.

Mesenchymal stem cells (MSCs), such as bone marrow derived MSCs are identified and isolated following the standard methods (Soleimani and Nadri. Nature Protocols 2009; 4(1):102-6.). Briefly, bone marrow is flushed out the bone with cut ends with DMEM+10% FBS. The cell suspension is filtered through a 70 mm mesh. MSCs are cultured in 100 mm dishes in 1 ml at a density of $25 \times 10^6$ cells/ml, and incubated at 37° C. with 5% $CO_2$ in a humidified chamber. After 3 hours, nonadherent cells are removed and the medium is replaced with fresh DMEM+10% FBS. Culture medium is replaced every 8 hours, for up to 72 hours of culture, and then replaced every 3 days thereafter. Adherent cells are designated as MSCs, at passage 0, and will exhibit a spindle-shaped morphology. Based on flow cytometry, MSCs will express Stro-1, CD271, SSEA-4, CD146, CD105, CD73, and CD90, and negative for CD45, CD34, CD14, CD11b, CD79a [Kohler et al. Aging Cell, 12(6):988-999].

Example 3

CITED2 reprogrammed stem cells slow disease progression and relieve pain in tendinopathy: Using a well-established Achilles tendinopathy model [5], the action of CITED2-modulated TSPCs was examined on improved pathogenesis and symptoms of tendinopathy, and tendon mechanical properties and function.

Methods: Human TSPCs (hTSPCs) were isolated from biceps brachii tendons of patients (62-68 yrs) undergoing total shoulder replacement (n=6) and used at passage 3 or below. TSPCs ($5 \times 10^5$) were transfected with either plasmid containing CITED2 cDNA or a vector control and injected into the site of tendinopathy in the Achilles, 3 days after collagenase-induced tendinopathy (Sprague Dawley rats, 5-6 months, male), according to IACUC protocol. Four weeks after tendinopathy induction, von Frey testing examined mechanical allodynia to assess pain [6]. At sacrifice, samples were harvested for histology (H&E) and immunohistochemistry (n=3/group), mechanical testing (n=6/group), and RT-qPCR analysis (n=6/group) for genes of pro-inflammatory cytokines and mediators related to matrix degradation and neurovascularization in tendinopathy. An ANOVA with Tukey post-hoc test was utilized to determine statistical significance.

Figure 16A:
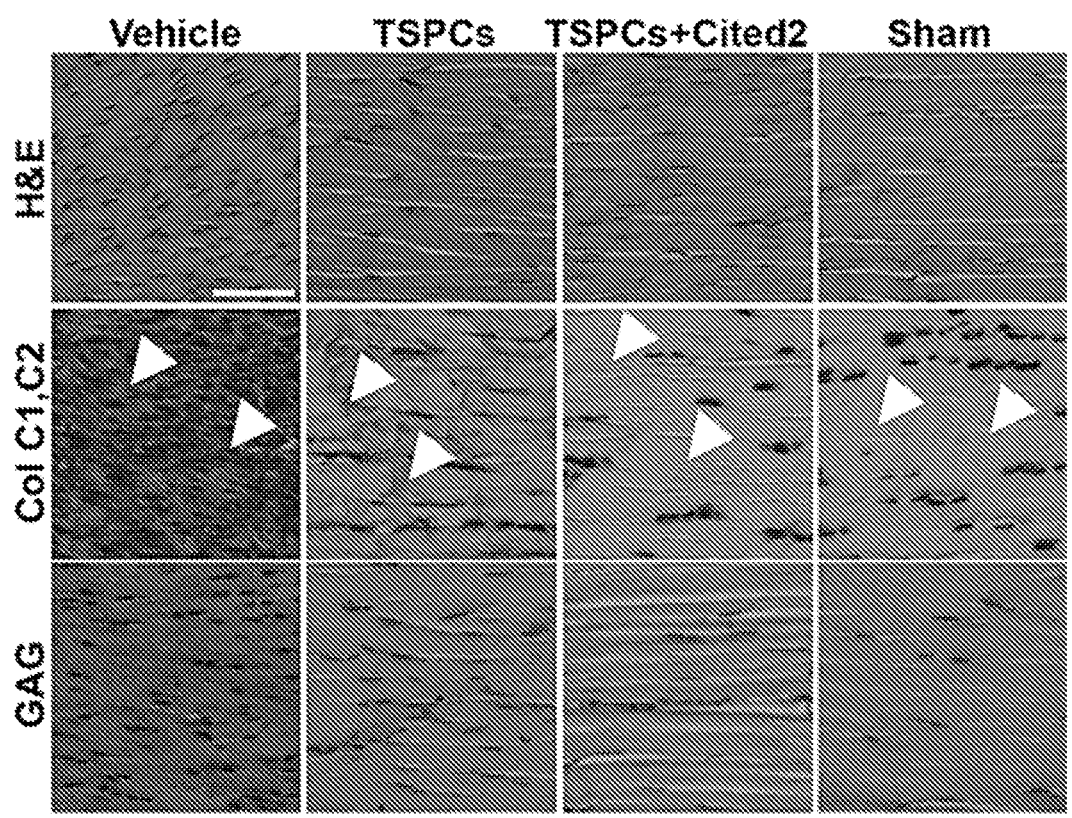
FIG. 16A-C: (A) H&E, IHC for cleaved collagen (Col1C1, C2 [see arrowheads]), and Safranin O staining (red color) for GAGs. Scale bar=100 μm. (B) IHC for Col1a1 and Col3a1 (staining of extracellular matrix). (C) Gene expression analysis of Cited2, pro-inflammatory cytokines/mediators, neurovascularization-related factors, and genes involved in matrix synthesis and degradation. *=p<0.05 vs Sham (dotted line) or indicated comparison.
Figure 16B:
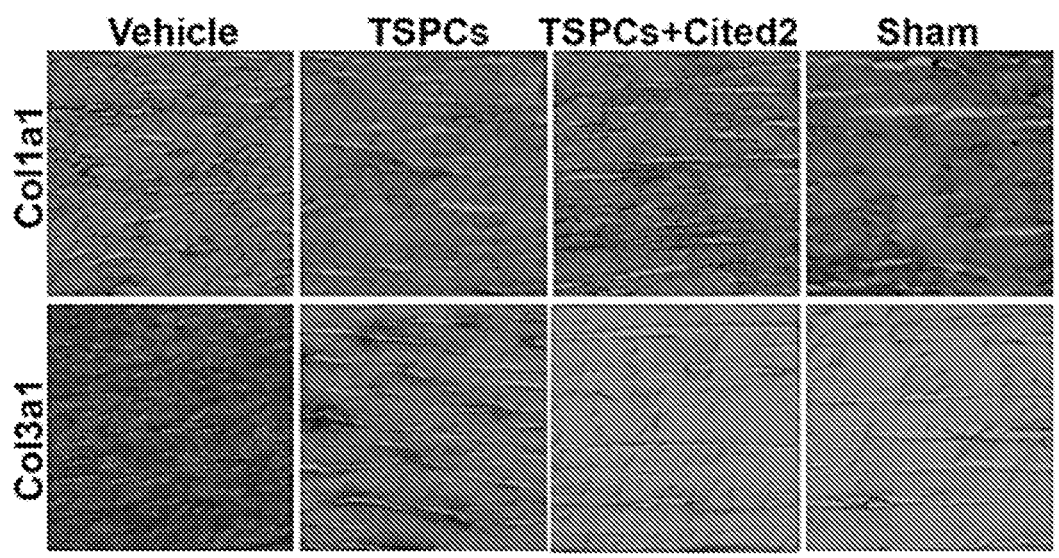
Figure 16C:
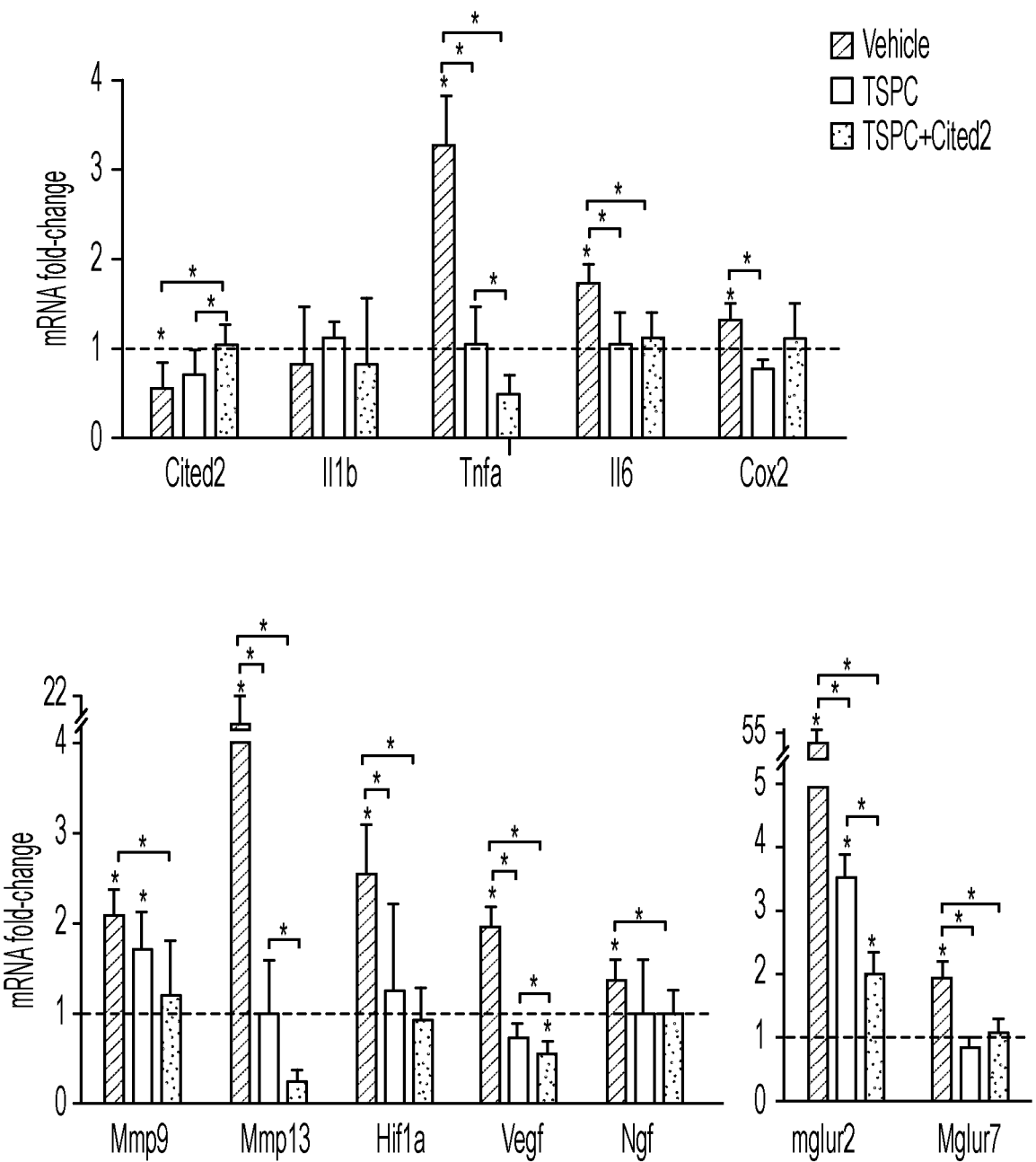
Figure 17A:
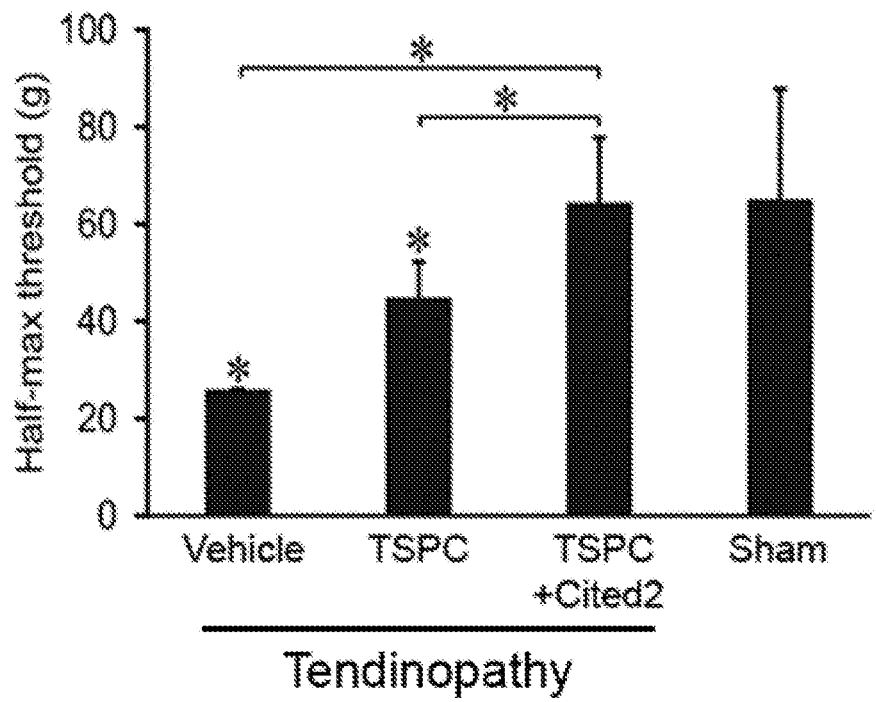
FIG. 17A-B: (A) von Frey pain assessment and (B) and gene expression of pro-inflammatory and pain mediators in DRG. * p<0.05 vs sham (dotted line in [B]) or indicated comparison.
Figure 17B:
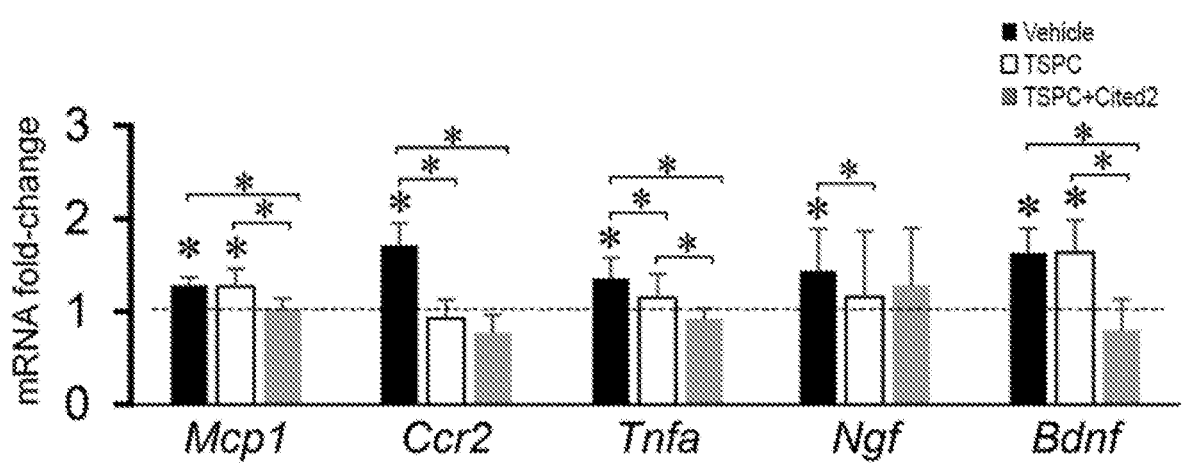
Figure 18A:
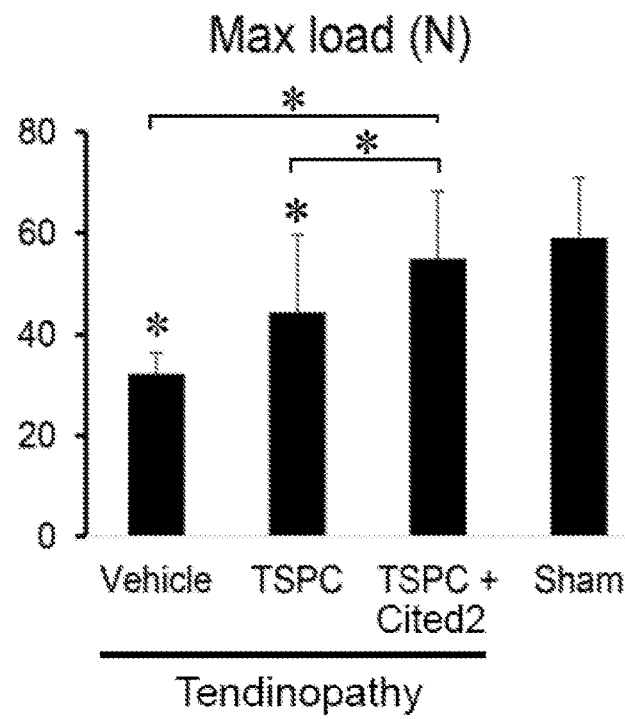
FIG. 18A-B: (A) Max load and (B) maximum stress. * p<0.05 vs sham or indicated comparison.
Figure 18B:
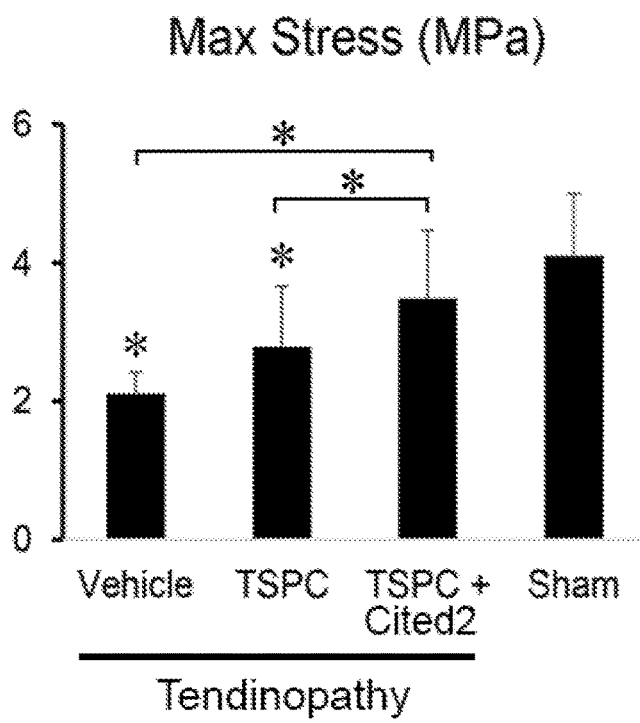

Results: Tendon tissue injected with TSPCs exhibited disease and symptom improvement compared with the vehicle control, while treatment with TSPCs overexpressed with CITED2 exhibited improved histology, immunohistochemistry and mechanical properties, similar to sham controls, with reduced pain/functional behavior. Specifically, the disease site of the TSPC+CITED2 group had: 1) improved morphology with reduced cellularity, better alignment of cell and matrix fibers, reduced collagen cleavage (Col1C1, C2), reduced GAG content (FIG. 16A), increased Col1a1 and reduced Col3a1 staining (FIG. 16B), and a significant reduction in gene expression for genes such as Tnfa, Mmp9 and 13 (pro-inflammatory cytokines/mediators), Hif1a, Vegf (vascularization) and Ngf, Bdnf, mglur2, and mglur7 (nerve ingrowth); 2) pain relief, as indicated by reduced sensitivity to mechanical insult (mechanical allodynia), and reduced expression of neuropathic-related transmitters in the dorsal root ganglion (DRG), which contains bodies of sensory neurons innervating the Achilles tendon; (FIG. 17; 18) improved Achilles tendon mechanical properties as indicated by a higher maximum load (FIG. 18A) and maximum stress (FIG. 18B).

Thus it was demonstrated that CITED2-modulated stem cell treatment significantly improves not only tendinopathy pathology, but also the mechanical properties of the tendon, and relieved pain symptoms in a rat Achilles tendinopathy model. CITED2 modulates a panel of genes that are highly relevant to tendinopathy progression and symptom development, supporting its therapeutic effect for tendinopathy.

REFERENCES

1. Magnusson et al. Nature Rev Rheum, 2010.
2. Cook and Purdam. Br J Sports Med. 2013.
3. Zhou et al. Aging Cell, 2010.
4. Saad et al. ORS 2013.
5. Chen et al. Cell Physiol Biochem, 2014.
6. Leong et al. Arthritis Res Ther, 2014.

What is claimed is:

1. A method of treating a tendinopathy in a subject comprising administering to the subject tendon stem/progenitor cells (TSPCs) transduced or transfected with a vector comprising CREB-binding protein/p300-interacting protein 2 (CITED2) cDNA, wherein the TSPCs are administered to the site of the tendinopathy in an amount effective to treat the tendinopathy in the subject, and wherein the subject does not have a ruptured tendon.

2. The method of claim 1, wherein the TSPCs have been obtained from a human prior to their transduction or transfection.

3. The method of claim 1, wherein the TSPCs have been obtained from a human biceps brachii tendon.

4. The method of claim 1, wherein the tendinopathy is of an Achilles tendon, a knee tendon or an arm tendon.

5. The method of claim 1, wherein the tendinopathy comprises a tendinosis or a tendonitis.

6. The method of claim 1, wherein the subject is a human.

* * * * *

SEQUENCE LISTING

```
<160> NUMBER OF SEQ ID NOS: 2

<210> SEQ ID NO 1
<211> LENGTH: 270
<212> TYPE: PRT
<213> ORGANISM: Homo sapiens

<400> SEQUENCE: 1

Met Ala Asp His Met Met Ala Met Asn His Gly Arg Phe Pro Asp Gly
1               5                   10                  15

Thr Asn Gly Leu His His His Pro Ala His Arg Met Gly Met Gly Gln
            20                  25                  30

Phe Pro Ser Pro His His His Gln Gln Gln Gln Pro Gln His Ala Phe
        35                  40                  45

Asn Ala Leu Met Gly Glu His Ile His Tyr Gly Ala Gly Asn Met Asn
    50                  55                  60

Ala Thr Ser Gly Ile Arg His Ala Met Gly Pro Gly Thr Val Asn Gly
65                  70                  75                  80
```

Gly His Pro Pro Ser Ala Leu Ala Pro Ala Arg Phe Asn Asn Ser
                85                  90                  95

Gln Phe Met Gly Pro Pro Val Ala Ser Gln Gly Gly Ser Leu Pro Ala
            100                 105                 110

Ser Met Gln Leu Gln Lys Leu Asn Asn Gln Tyr Phe Asn His His Pro
            115                 120                 125

Tyr Pro His Asn His Tyr Met Pro Asp Leu His Pro Ala Ala Gly His
            130                 135                 140

Gln Met Asn Gly Thr Asn Gln His Phe Arg Asp Cys Asn Pro Lys His
145                 150                 155                 160

Ser Gly Gly Ser Ser Thr Pro Gly Gly Ser Gly Ser Ser Thr Pro
                165                 170                 175

Gly Gly Ser Gly Ser Ser Gly Gly Ala Gly Ser Ser Asn Ser
            180                 185                 190

Gly Gly Gly Ser Gly Ser Gly Asn Met Pro Ala Ser Val Ala His Val
            195                 200                 205

Pro Ala Ala Met Leu Pro Pro Asn Val Ile Asp Thr Asp Phe Ile Asp
            210                 215                 220

Glu Glu Val Leu Met Ser Leu Val Ile Glu Met Gly Leu Asp Arg Ile
225                 230                 235                 240

Lys Glu Leu Pro Glu Leu Trp Leu Gly Gln Asn Glu Phe Asp Phe Met
                245                 250                 255

Thr Asp Phe Val Cys Lys Gln Gln Pro Ser Arg Val Ser Cys
            260                 265                 270

<210> SEQ ID NO 2
<211> LENGTH: 275
<212> TYPE: PRT
<213> ORGANISM: Homo sapiens

<400> SEQUENCE: 2

Met Ser Gly Leu Glu Met Ala Asp His Met Met Ala Met Asn His Gly
1               5                   10                  15

Arg Phe Pro Asp Gly Thr Asn Gly Leu His His His Pro Ala His Arg
            20                  25                  30

Met Gly Met Gly Gln Phe Pro Ser Pro His His His Gln Gln Gln Gln
        35                  40                  45

Pro Gln His Ala Phe Asn Ala Leu Met Gly Glu His Ile His Tyr Gly
        50                  55                  60

Ala Gly Asn Met Asn Ala Thr Ser Gly Ile Arg His Ala Met Gly Pro
65                  70                  75                  80

Gly Thr Val Asn Gly Gly His Pro Pro Ser Ala Leu Ala Pro Ala Ala
                85                  90                  95

Arg Phe Asn Asn Ser Gln Phe Met Gly Pro Pro Val Ala Ser Gln Gly
            100                 105                 110

Gly Ser Leu Pro Ala Ser Met Gln Leu Gln Lys Leu Asn Asn Gln Tyr
            115                 120                 125

Phe Asn His His Pro Tyr Pro His Asn His Tyr Met Pro Asp Leu His
            130                 135                 140

Pro Ala Ala Gly His Gln Met Asn Gly Thr Asn Gln His Phe Arg Asp
145                 150                 155                 160

Cys Asn Pro Lys His Ser Gly Gly Ser Ser Thr Pro Gly Gly Ser Gly
                165                 170                 175

Gly Ser Ser Thr Pro Gly Gly Ser Gly Ser Ser Ser Gly Gly Gly Ala
            180                 185                 190

```
Gly Ser Ser Asn Ser Gly Gly Gly Ser Gly Ser Gly Asn Met Pro Ala
        195             200             205

Ser Val Ala His Val Pro Ala Ala Met Leu Pro Pro Asn Val Ile Asp
    210             215             220

Thr Asp Phe Ile Asp Glu Glu Val Leu Met Ser Leu Val Ile Glu Met
225             230             235             240

Gly Leu Asp Arg Ile Lys Glu Leu Pro Glu Leu Trp Leu Gly Gln Asn
                245             250             255

Glu Phe Asp Phe Met Thr Asp Phe Val Cys Lys Gln Gln Pro Ser Arg
                260             265             270

Val Ser Cys
        275
```